US011516617B2

United States Patent
Barroso et al.

(10) Patent No.: US 11,516,617 B2
(45) Date of Patent: Nov. 29, 2022

(54) SYSTEM AND METHOD FOR FACILITATING A USER INTERFACE VIA DEVICE-ON PREMISE DETECTION AND EVENT GENERATION BASED THEREON

(71) Applicant: KONINKLIJKE PHILIPS N.V., Eindhoven (NL)

(72) Inventors: Andre Melon Barroso, Aachen (DE); Gijs Geleijnse, Geldrop (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 738 days.

(21) Appl. No.: 15/432,033

(22) Filed: Feb. 14, 2017

(65) Prior Publication Data
US 2017/0262592 A1    Sep. 14, 2017

Related U.S. Application Data

(60) Provisional application No. 62/307,874, filed on Mar. 14, 2016.

(51) Int. Cl.
*H04W 4/02* (2018.01)
*G16H 40/20* (2018.01)
*H04W 4/029* (2018.01)

(52) U.S. Cl.
CPC .............. *H04W 4/02* (2013.01); *G16H 40/20* (2018.01); *H04W 4/029* (2018.02)

(58) Field of Classification Search
None
See application file for complete search history.

(56) References Cited

U.S. PATENT DOCUMENTS

| | | | |
|---|---|---|---|
| 6,047,259 A * | 4/2000 | Campbell | G16H 40/20 705/3 |
| 8,779,924 B2 * | 7/2014 | Pesot | A61B 5/0006 340/573.1 |

(Continued)

FOREIGN PATENT DOCUMENTS

| | | |
|---|---|---|
| KR | 100692803 B1 | 3/2007 |
| WO | WO2014064053 A2 * | 5/2014 |
| WO | 2015123540 A1 | 8/2015 |

OTHER PUBLICATIONS

F. Naya, H. Noma, R. Ohmura and K. Kogure, "Bluetooth-based indoor proximity sensing for nursing context awareness," Ninth IEEE International Symposium on Wearable Computers (ISWC'05), 2005, pp. 212-213, doi: 10.1109/ISWC.2005.13. (Year: 2005).*

*Primary Examiner* — Paul R Fisher

(57) ABSTRACT

The present disclosure pertains to a system configured to facilitate a user interface via device-on-premise detection and event generation based thereon. The system comprises a computer system configured to: obtain, from beneficiary user devices, event information indicating events corresponding to device-on-premise detections of the beneficiary user devices, each of the device-on-premise detections comprising a detection of a location of a beneficiary user device overlapping with a location of at least one service facility premise of a predefined set of premises; determine a consultant that is to be at a service facility premise; determine, based on the event information, a set of beneficiaries at the service facility premise; obtain service information indicating health services previously provided to or requested by the set of beneficiaries; and generate, based on the set of beneficiaries and the service information, at least a portion of a user interface indicating beneficiaries to be identified to the consultant.

17 Claims, 5 Drawing Sheets

(56) References Cited

U.S. PATENT DOCUMENTS

| | | | |
|---|---|---|---|
| 2004/0059205 A1 | 3/2004 | Carlson et al. | |
| 2004/0152961 A1 | 8/2004 | Carlson et al. | |
| 2005/0242928 A1* | 11/2005 | Kirkeby | G08B 5/22 340/286.07 |
| 2008/0059227 A1 | 3/2008 | Clapp | |
| 2009/0091458 A1* | 4/2009 | Deutsch | G16H 40/20 705/2 |
| 2011/0105854 A1* | 5/2011 | Kiani | G16H 40/63 600/300 |
| 2014/0012597 A1* | 1/2014 | Nolte | G06Q 10/10 705/3 |
| 2015/0213202 A1 | 7/2015 | Amarasingham et al. | |

* cited by examiner

SYSTEM AND METHOD FOR FACILITATING A USER INTERFACE VIA DEVICE-ON PREMISE DETECTION AND EVENT GENERATION BASED THEREON

CROSS-REFERENCE TO PRIOR APPLICATIONS

This application claims the benefit of or priority of U.S. Provisional patent application Ser. No. 62/307,874, filed Mar. 14, 2016, all of which are incorporated herein in whole by reference.

BACKGROUND

1. Field

The present disclosure pertains to a system and method for facilitating a user interface via device-on-premise detection and event generation based thereon.

2. Description of the Related Art

With the advent of healthcare technologies and modern medicine, and the increase in access to health services, developed and emerging countries alike have undergone transformational demographic change as fertility rates decline and life expectancy rises. Such transformation has reshaped the health profile of the population as chronic diseases related to aging and lifestyle are becoming increasingly more prevalent. Although mobile devices (e.g., tablets, smartphones, etc.) have become ubiquitous, typical health systems fail to utilize such devices in various ways, for example, to improve the health of individuals. These and other drawbacks exist.

SUMMARY

Accordingly, one or more aspects of the present disclosure relate to a system configured to facilitate a user interface via device-on-premise detection and event generation based thereon. The system comprises a computer system comprising one or more physical processors configured to: obtain, from one or more beneficiary user devices of one or more beneficiaries, event information indicating events corresponding to device-on-premise detections of the one or more beneficiary user devices, each of the device-on-premise detections comprising a detection by at least one of the one or more beneficiary user devices of a location of the at least one beneficiary user device overlapping with a location of at least one service facility premise of a predefined set of service facility premises; determine a consultant that is to be at a first service facility premise of the predefined set of service facility premises; determine, based on the event information, a set of beneficiaries that are currently at the first service facility premise; obtain service information indicating one or more health services previously provided to or requested by beneficiaries of the set of beneficiaries; and generate, based on the set of beneficiaries and the service information, at least a portion of a user interface indicating beneficiaries to be identified to the consultant.

Another aspect of the present disclosure relates to a method for facilitating a user interface via device-on-premise detection and event generation based thereon, where the method is implemented at least in part by a computer system comprising one or more physical processors configured by machine-readable instructions which, when executed, perform the method. The method comprises obtaining, from one or more beneficiary user devices of one or more beneficiaries, event information indicating events corresponding to device-on-premise detections of the one or more beneficiary user devices, each of the device-on-premise detections comprising a detection by at least one of the one or more beneficiary user devices of a location of the at least one beneficiary user device overlapping with a location of at least one service facility premise of a predefined set of service facility premises; determining a consultant that is to be at a first service facility premise of the predefined set of service facility premises; determining, based on the event information, a set of beneficiaries that are currently at the first service facility premise; obtaining service information indicating one or more health services previously provided to or requested by beneficiaries of the set of beneficiaries; and generating, based on the set of beneficiaries and the service information, at least a portion of a user interface indicating beneficiaries to be identified to the consultant.

Still another aspect of present disclosure relates to a system configured to facilitate a user interface via device-on-premise detection and event generation based thereon. The system comprises means for obtaining, from one or more beneficiary user devices of one or more beneficiaries, event information indicating events corresponding to device-on-premise detections of the one or more beneficiary user devices, each of the device-on-premise detections comprising a detection by at least one of the one or more beneficiary user devices of a location of the at least one beneficiary user device overlapping with a location of at least one service facility premise of a predefined set of service facility premises; means for determining a consultant that is to be at a first service facility premise of the predefined set of service facility premises; means for determining, based on the event information, a set of beneficiaries that are currently at the first service facility premise; means for obtaining service information indicating one or more health services previously provided to or requested by beneficiaries of the set of beneficiaries; and means for generating, based on the set of beneficiaries and the service information, at least a portion of a user interface indicating beneficiaries to be identified to the consultant.

These and other objects, features, and characteristics of the present disclosure, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the disclosure.

DETAILED DESCRIPTION OF EXEMPLARY EMBODIMENTS

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other. As used herein, "or" means "and/or" unless the context clearly dictates otherwise.

As used herein, "beneficiary" means (i) an individual who is seeking medical treatment of other health services, (ii) an individual who is registered to receive or is receiving medical treatment or other health services, (iii) an individual targeted for or otherwise identified as needing medical treatment or other health services (e.g., based on risk factors, such as age, smoking status, or other risk factors), or (iv) other individual who may receive benefits. As used herein, "consultant" means an individual who provides services or information regarding such services to another individual.

Figure 1:
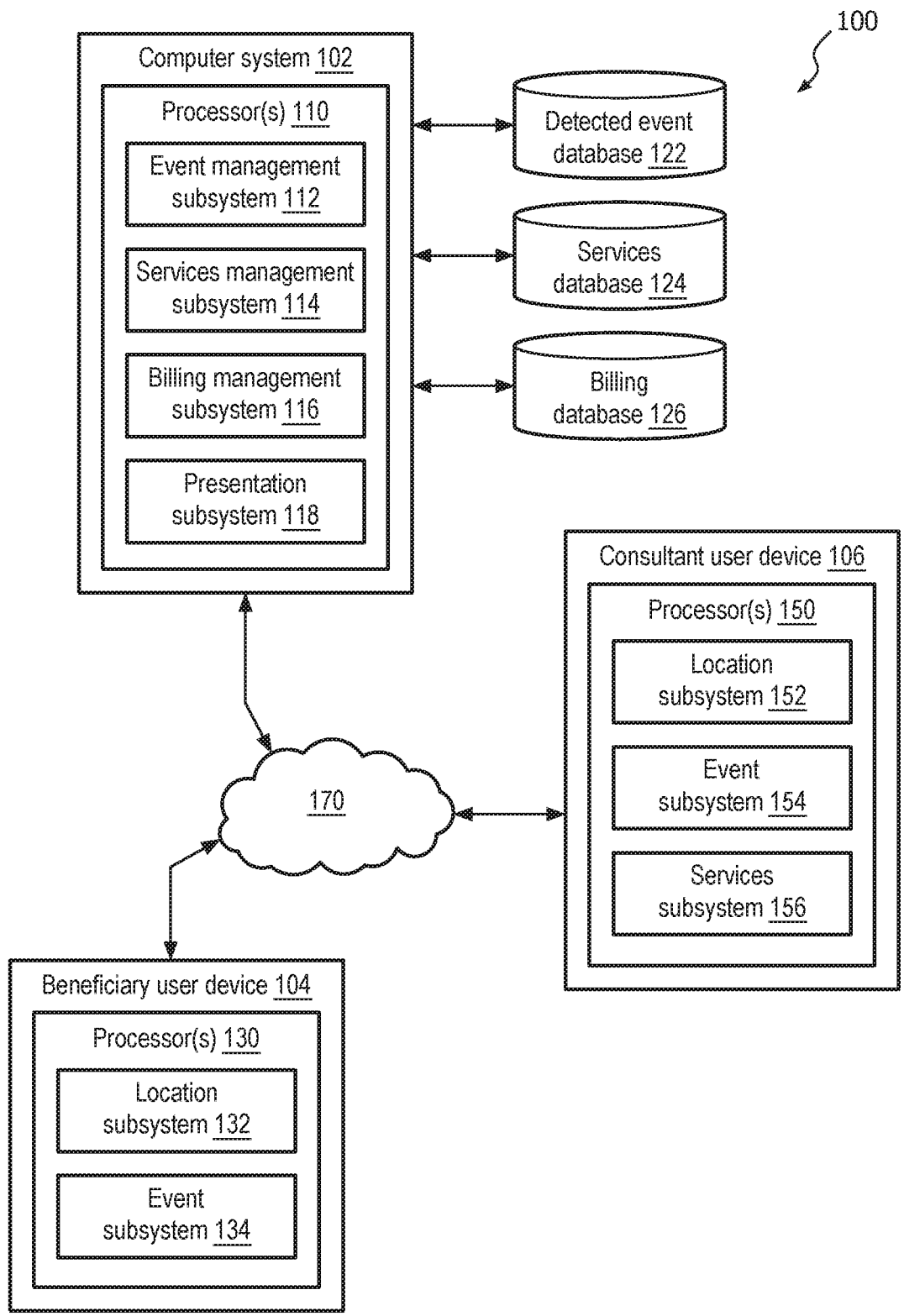
FIG. 1 is a schematic illustration of a system configured to facilitate a user interface, in accordance with one or more embodiments.

FIG. 1 shows a system 100 for facilitating a user interface, in accordance with one or more embodiments. In certain embodiments, system 100 may provide timely and personalized information on who is at risk and who can benefit from primary care services or other health services. As an example, system 100 may facilitate management of risks at an early stage of a health condition, before complications arise and when interventions are more likely to alter the course of events. As another example, system 100 may personalize assignment of risks to individuals within a population. As yet another example, system 100 may assign and track, at the individual level, resources for intelligence gathering.

As shown in FIG. 1, in an embodiment, system 100 may comprise a computer system 102 (e.g., one or more servers or other computing devices). Computer system 102 may comprise an event management subsystem 112, a services management subsystem 114, a billing management subsystem 116, a presentation subsystem 118, or other components.

System 100 may further comprise one or more user devices, such as one or more beneficiary user devices 104, one or more consultant user devices 106, or other user devices. The user devices may comprise any type of mobile terminal, fixed terminal, or other device. By way of example, the user devices may comprise desktop computers, notebook computers, tablet computer, smartphones, wearable devices, or other user devices. Users may, for instance, utilize one or more user devices 104 or 106 to interact with computer system 102 or other components of system 100. It should be noted that, while one or more operations are described herein as being performed by components of computer system 102, those operations may, in some embodiments, be performed by components of user device 104 or 106 or other components of system 100.

Beneficiary user device 104 may comprise a location subsystem 132, an event subsystem 134, or other components. Consultant user device 106 may comprise a location subsystem 152, an event subsystem 154, a services subsystem 156, or other components. It should be noted that, while one or more operations are described herein as being performed by components of one of user devices 104 or 106, those operations may, in some embodiments, be performed by components of the other one of user devices 104 or 106 or other components of system 100.

In some embodiments, computer system 102 may provide a user interface for a consultant, where the user interface indicates one or more beneficiaries at a service facility premise that are to be visited by a consultant at the service facility premise. The user interface (and portions thereof) may be generated based on (i) event information obtained from one or more beneficiary user devices 104; (ii) service information indicating one or more health services previously provided to or requested by the beneficiaries; or (iii) other information, as described herein.

In an embodiment, event management subsystem 112 may obtain event information, where the event information indicates events corresponding to device-on-premise detections of one or more beneficiary user devices (e.g., beneficiary user devices 104) of one or more beneficiaries (e.g., patients or other beneficiaries), events corresponding to device-off-premise detections of the beneficiary user devices, or other events. Event management subsystem 112 may, for example, obtain the event information from the beneficiary user devices (e.g., smartphones of the beneficiaries or other user devices of the beneficiaries). As an example, each device-on-premise detection may comprise a detection by at least one of the beneficiary user devices of a location of the at least one beneficiary user device overlapping with a location of at least one service facility premise of a predefined set of service facility premises. Each device-off-premise detection may comprise a detection by at least one of the beneficiary user devices of a location of the at least one beneficiary user device (just detected to be overlapping) no longer overlapping with a location of at least one service premise of the predefined set of service facility premises. In an embodiment, the event information may be stored in detected event database 122 and subsequently obtained from detected event database 122 by event management subsystem 112.

In an embodiment, the event information may additionally or alternatively comprise location information (e.g., latitude/longitude coordinates, cell identification information, WiFi positioning information, etc.) indicating the location at which a user device is detected, time information (e.g., timestamp) indicating the time at which the user device is detected at that location, identifier information (e.g., a unique identifier of the beneficiary who is logged into the user device) indicating an identifier of the beneficiary, or other information.

In an embodiment, beneficiary user device 104 may obtain its location via its location subsystem 132 (e.g., comprising a global positioning system (GPS) module, a WiFi positioning module, a cell identification module, etc.) at a first time. In an embodiment, upon obtaining its location, event subsystem 134 of beneficiary user device 104 may detect that the obtained location (of beneficiary user device 104) overlaps with a location of at least one service facility premise of a predefined set of service facility premises. Responsive to the detection, event subsystem 134 may generate an event corresponding to the detection, where the event indicates that beneficiary user device 104 is detected at the overlapping location at the first time. Event subsystem 134 may generate event information to indicate the corresponding event, and provide the event information to computer system 102.

In an embodiment, after detecting that a location of beneficiary user device 104 overlapped with a location of a service facility premise, event subsystem 134 of beneficiary user device 104 may detect that the location of beneficiary user device 104 (at another time) no longer overlaps with a location of at least one service facility premise of a predefined set of service facility premises. Responsive to the detection, event subsystem 134 may generate an event corresponding to the detection, where the event indicates that the location of beneficiary user device 104 at the other time no longer overlaps with the location of the service facility premise. Event subsystem 134 may generate event information to indicate the corresponding event, and provide the event information to computer system 102.

In an embodiment, a predefined set of service facility premises (and/or their respective locations or other related information) may be stored at beneficiary user device 104 in its internal persistent storage. In one use case, event subsystem 134 of beneficiary user device 104 may compare the current location of beneficiary user device 104 with the locations of the service facility premises of the predefined set stored at beneficiary user device 104. When event subsystem 134 detects (based on the comparison) that the current location of beneficiary user device 104 overlaps (or no longer overlaps) with one of the locations of those service facility premises, event subsystem 134 may generate an event corresponding to the detection. In an embodiment, the event subsystem 134 of beneficiary user device 104 may provide event information (indicating generated events) to computer system 102 when beneficiary user device 104 is connected to the Internet, on a periodic basis (e.g., every minute, every hour, every day, or other periodic basis), or via one or more other triggers.

In an embodiment, event subsystem 134 may dynamically update the predefined set of service facility premises stored at beneficiary user device 104. As an example, event subsystem 134 may dynamically update the predefined set of service facility premises based on the current location of beneficiary user device 104. In this way, for example, beneficiary user device 104 need not necessarily store the complete list of known service facility premises, reducing the size of the predefined set of service facility premises and information associated therewith (e.g., location information, a list of services offered at each service facility, or other information). As another example, by maintaining a subset of the complete list of known service facility premises at beneficiary user device 104, event subsystem 134 may perform detection of overlapping/non-overlapping conditions (e.g., when the current location of beneficiary user device 104 overlaps or no longer overlaps with one of the predefined service facility premises) without necessarily being connected to the Internet, and generate event information indicating events corresponding to such detection that can later be provided to computer system 102. As yet another example, by maintaining a smaller subset that is dynamically updated based on the current location of beneficiary user device 104 (e.g., when beneficiary user device 104 is connected to the Internet, on a periodic basis, or via other triggers), event subsystem 134 may perform faster, more efficient comparisons of the current location of beneficiary user device 104 and the locations of the service facility premises of the predefined subset.

In an embodiment, a predefined set of service facility premises (and/or their respective locations) may be stored at computer system 102 or other system (e.g., a remote storage system). In one scenario, event subsystem 134 of beneficiary user device 104 may compare the current location of beneficiary user device 104 with the locations of the service facility premises of the predefined set (stored at computer system 102 or other system) to detect overlapping/non-overlapping conditions. In another scenario, event subsystem 134 may provide the current location of beneficiary user device 104 to computer system 102, after which computer system 102 may perform comparisons of the current location of beneficiary user device 104 with the locations of the service facility premises of the predefined set (stored at computer system 102 or other system) to detect overlapping/non-overlapping conditions.

In an embodiment, services management subsystem 114 may determine a consultant that is to be at a first service facility premise of the predefined set of service facility premises. In an embodiment, event management subsystem 112 may determine, based on event information (e.g., indicating events corresponding to overlapping/non-overlapping conditions), a set of beneficiaries that are currently at the first service facility premise.

Figure 2:
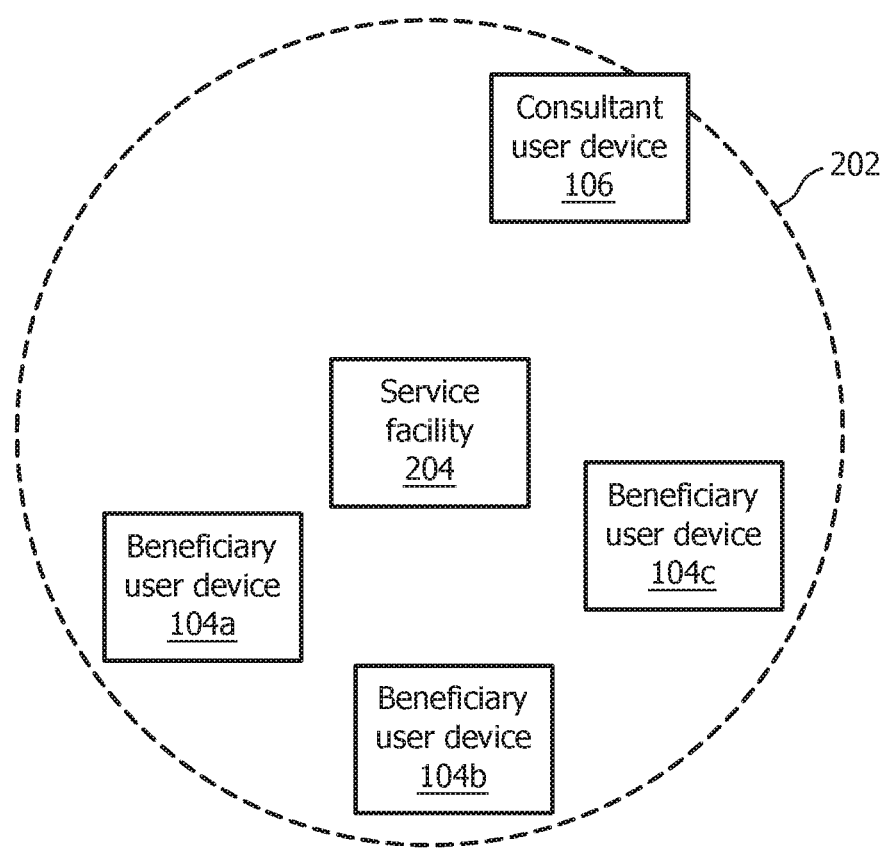
FIG. 2 illustrates a use case of device-on-premise detection and event generation based thereon, in accordance with one or more embodiments.

In an embodiment, services management subsystem 114 may determine that the consultant is to be at the first service facility premise based on the consultant's user device 106 coming within the premise of the first service facility. In one use case, with respect FIG. 2, responsive to detecting the consultant's user device 106 within premise 202 of service facility 204 or within proximity of service facility premise 202, services management subsystem 114 may determine that the consultant is at service facility premise 202 to visit one or more beneficiaries. As an example, responsive to obtaining location information from consultant user device 106 (e.g., indicating that the current location of consultant user device 106 overlaps with a location of service facility premise 202), event management subsystem 112 may determine that the consultant is at service facility premise 202, and forward such determination to services management subsystem 114. Based on such determination, services management subsystem 114 may predict that the consultant is at service facility premise 202 to visit one or more beneficiaries.

In an embodiment, services management subsystem 114 may determine that the consultant is to be at the first service facility premise based on scheduling information associated with the consultant. As an example, if the consultant's calendar includes one or more appointments, meetings, tasks, etc., at the first service facility, services management subsystem 114 may predict based on the consultant's calendar information that the consultant is to be the first service facility premise to visit one or more beneficiaries. In one use case, the scheduling information may be stored at services database 124, and services management subsystem 114 may obtained the scheduling from services database 124 to perform such predictions.

In an embodiment, billing management subsystem 116 may obtain service information indicating one or more health services previously provided to or requested by beneficiaries (of a set of beneficiaries determined to be at a service facility premise). As an example, service information associated with the beneficiaries may be stored at billing database 126, and billing management subsystem 116 may obtain the service information from billing database 126.

The service information may comprise identification information associated with each beneficiary (e.g., a unique identifier of the beneficiary), information indicating a health service provided to or requested by the beneficiary (e.g., a code indicating a clinical service provided to the beneficiary, a code indicating a clinical service requested by the beneficiary, but denied to the beneficiary at the time, etc.), time information associated with the provided health service (e.g., a timestamp indicating the date/time at which the clinical service was provided to the beneficiary), or other information. In one scenario, the service information for each beneficiary may comprise one or more bills or invoices for the beneficiary that indicates the identification information, the information indicating the provided health service, the time information, or other information for the beneficiary.

In an embodiment, billing management subsystem 116 may obtain the service information (indicating the health services previously provided to or requested by the beneficiaries) responsive to determining that the beneficiaries are at the service facility premise. As an example, with respect to FIG. 2, at one or more respective times, each of the beneficiary user devices 104a-104c may detect that its current location overlaps with a location of service facility premise 202 and, in response, generate an event corresponding to the detection such that the generated event indicates that the respective user (i.e., one of the beneficiaries) of the beneficiary user device 104 is at service facility premise at the respective times. Each of the beneficiary user devices 104a-104c may provide their respective generated events as event information to computer system 102, which is then obtained by event management subsystem 112. Responsive to event management subsystem 112 determining from the obtained event information that the beneficiaries are at service facility premise 202, billing management subsystem 116 may obtain the service information for those beneficiaries from billing database 126.

In an embodiment, presentation subsystem 118 may generate at least a portion of a user interface indicating beneficiaries to be identified to the consultant. In an embodiment, presentation subsystem 118 may generate the user interface (or the user interface portion) based on the set of beneficiaries (determined based on the event information), the service information (obtained indicating health services previously provided to or requested by the set of beneficiaries), or other information. As an example, with respect to FIG. 3, user interface 300 may be generated to comprise one or more indications of individuals for the consultant to visit (e.g., beneficiaries of "Service Facility Premise A" that are beneficiaries of a health plan or other individuals), and provided to the consultant's user device 106. As another example, actionable areas 302-310 may be generated on user interface 300 based on the set of beneficiaries, the service information, or other information. Actionable areas 302-310 may, for instance, comprise actionable buttons or other interface items that may be activated (e.g., via a touch, hold, click, or other activation technique) to initiate one or more actions related to the respective actionable areas 302-310 (e.g., actions related to the indicated individuals). The actions (that may be initiated by activating an actionable interface item) may comprise obtaining additional details about an indicated individual (e.g., available services to be offered to the individual, the individual's personal information, the individual's medical history, the individual's insurance information, etc.), initiating scheduling of a meeting with the indicated individual (e.g., sending a message to the customer with one or more proposed dates/times for the meeting), or other actions.

In an embodiment, services subsystem 156 of consultant user device 106 may work with services management subsystem 114 of computer system to identify one or more health services (available to the individual) to the consultant. As an example, upon determining the beneficiaries (to be identified to the consultant), services management subsystem 114 of computer system 102 may provide information indicating the respective sets of health services available to the beneficiaries to services subsystem 156 of consultant user device 106. As a further example, with respect to FIG. 3, services subsystem 156 may display a respective set of health services available to a beneficiary on user interface 300 upon detecting user interaction with an actionable area (e.g., one of actionable areas 302-310) associated with the particular beneficiary (to which the set of health services is available).

Figure 3:
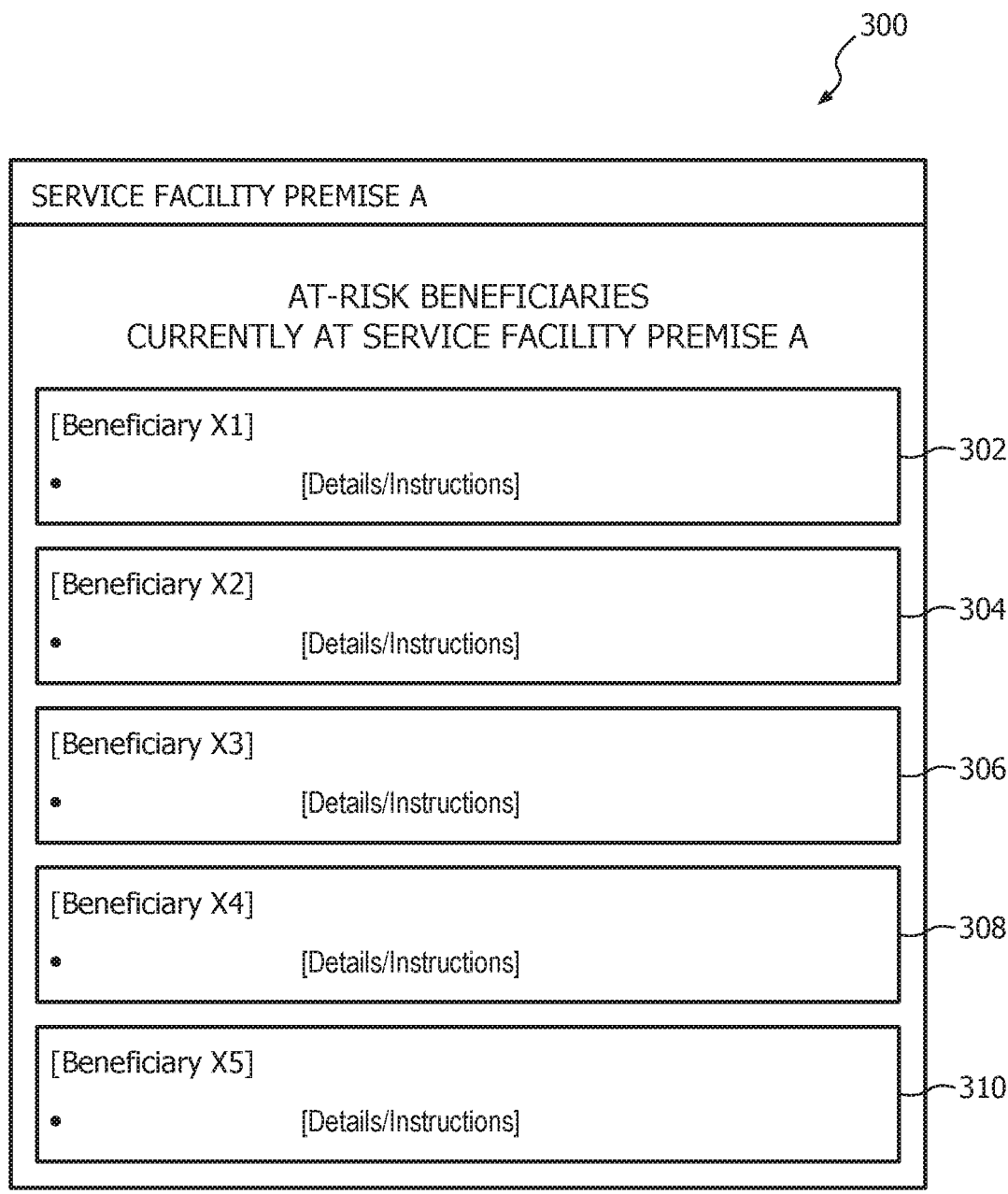
FIG. 3 illustrates a healthcare user interface provided via device-on-premise detection and event generation based thereon, in accordance with one or more embodiments.

In an embodiment, event management subsystem 112 may use event information (e.g., which indicates beneficiaries and the service facility premises at which they have been recently detected) to determine a set of beneficiaries that are at a service facility premise (e.g., "Service Facility Premise A" in FIG. 3). As an example, event management subsystem 112 may determine that a beneficiary is at the service facility premise responsive to the event information indicating that the beneficiary was detected at the service facility premise within the last 24 hours or other threshold time period. Services management system 114 may use service information (e.g., which indicates health services recently provided to beneficiaries) to prioritize the beneficiaries (of the determined beneficiary set) to be identified to a consultant that is at or will be at the service facility premise.

In an embodiment, for example, services management subsystem 114 may determine scores associated with the beneficiaries (of the set of beneficiaries determined to be at the service facility premise) based on the service information (e.g., which indicates health services recently provided to the beneficiaries). As an example, the determined scores may indicate respective relative correlations between health services previously provided to or requested by the beneficiaries of the set of beneficiaries and services available via the consultant (or an entity that the consultant is acting on behalf). As another example, presentation subsystem 118 may generate actionable areas associated with the beneficiaries such that the actionable areas are arranged on a user interface based on the determined scores (e.g., an actionable area associated with a beneficiary with a greater score may be placed higher or more prominently on the user interface than an actionable area associated with a beneficiary with a lower score, or other arrangement).

In one scenario, the beneficiaries (to be identified to the consultant) may be prioritized (and assigned respective priority scores) based on their respective objective needs for healthcare services available via the consultant (or an entity that the consultant is acting on behalf) (e.g., primary health care services offered by the consultant, primary healthcare services to which the consultant can refer the beneficiaries, or other healthcare services). For example, a bill for detailed electrocardiogram examination suggests that a beneficiary has cardiovascular issues and that the beneficiary's risk of complication may be controlled with education, physical activity, and periodic check-ups. As another example, a bill for a fasting plasma glucose test suggests that a beneficiary has diabetes and that the beneficiary's risks may also be managed by primary healthcare services. In a further scenario, presentation subsystem 118 may use the prioritization to generate actionable areas (related to at least a subset of the determined set of beneficiaries at the service facility premise) on a user interface such that the actionable areas are arranged in accordance with the respective priority scores associated with the beneficiaries.

In an embodiment, event management subsystem 112 may obtain event information that indicates events corresponding to device-on-premise detections of one or more consultant user devices (e.g., consultant user devices 106), events corresponding to device-off-premise detections of the consultant user devices, or other events. Event management subsystem 112 may, for example, obtain the event information from the consultant user devices (e.g., smartphones of the consultants or other user devices of the consultants). As an example, each device-on-premise detection may comprise a detection by at least one of the consultant user devices 106 of a location of the at least one consultant user device 106 overlapping with a location of at least one service facility premise of a predefined set of service facility premises. Each device-off-premise detection may comprise a detection by at least one of the consultant user devices 106 of a location of the at least one consultant user device (just detected to be overlapping) no longer overlapping with a location of at least one service premise of the predefined set of service facility premises. In an embodiment, the event information may be stored in detected event database 122 and subsequently obtained from detected event database 122 by event management subsystem 112.

In some embodiments, one or more operations are described herein as being performed by components of one of user devices 104 or 106, those operations may, in some embodiments, be performed by components of the other one of user devices 104 or 106 or other components of system 100. As an example, location subsystem 152 of consultant user device 106 may obtain a location of consultant user device 106 via one or more techniques utilized by beneficiary user device 104 (or its components) to obtain its location, including one or more such techniques described herein with respect to beneficiary user device 104. As another example, event subsystem 154 of consultant user device 106 may detect overlapping/non-overlapping conditions via one or more techniques utilized by beneficiary user device 104 (or its components) to detect overlapping/non-overlapping conditions, including one or more such techniques described herein with respect to beneficiary user device 104. As yet another example, event subsystem 154 of consultant user device 106 may store a predefined set of service facility premises (and/or their respective locations or other related information) in internal persistent storage of consultant user device 106, and/or dynamically update its stored predefined set of service facility premises (e.g., based the current location of consultant user device 106) via one or more techniques utilized by beneficiary user device 104 to dynamically its stored predefined set of service facility premises, including one or more such techniques described herein with respect to beneficiary user device 104.

In an embodiment, event management subsystem 112 may use event information obtained from consultant user devices 106 to generate coverage information related to respective consultants associated with consultant user device 106. As an example, the coverage information may comprise information indicating beneficiaries visited by the consultants or other information related to the visited beneficiaries. In one use case, for instance, the coverage information may indicate statistics on the dates/times that beneficiaries were visited by consultants, duration of such visits, or other attributes (e.g., number of visits in the last 12 months or other time period, average duration of the visits within a time period, etc.). In an embodiment, presentation subsystem 118 may generate a user interface (or a portion thereof) that graphically represents such statistics. As an example, presentation subsystem 118 may generate a user interface comprising a map such that respective portions of the map (e.g., buildings representing the various service facility premises visited by consultants) are color coded in accordance with the number of visits in the last 12 months or other time period, average duration of the visits within a time period, or other statistics.

Examples Flowcharts

Figure 4:
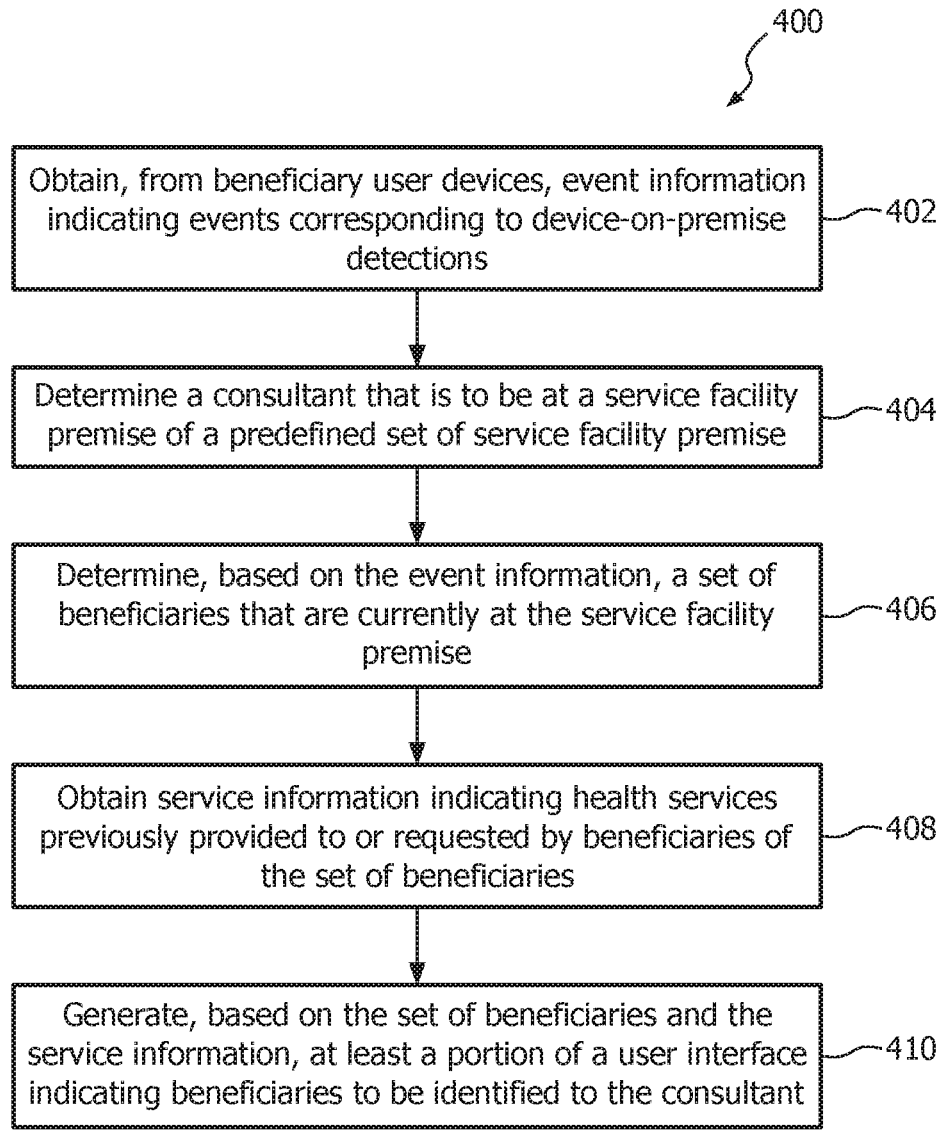
FIG. 4 illustrates a method for facilitating a user interface via device-on-premise detection and event generation based thereon, in accordance with one or more embodiments.
Figure 5:
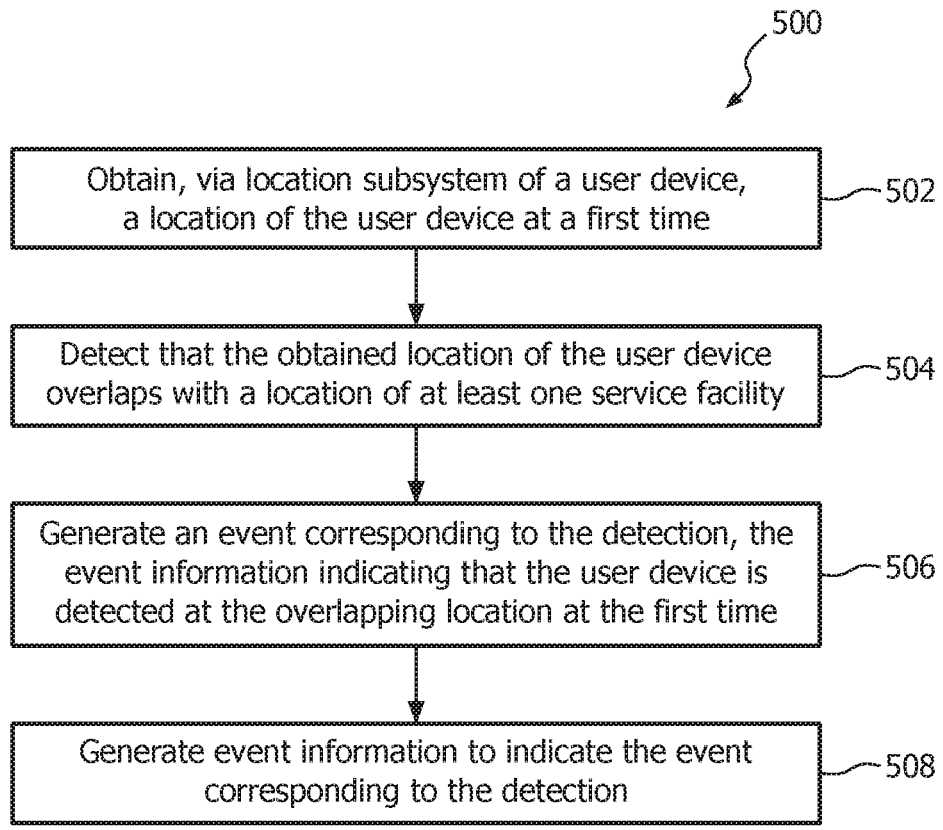
FIG. 5 illustrates a method for detecting overlap of a user device location and a service facility premise location and generating a corresponding event based thereon, in accordance with one or more embodiments.
Figure 6:
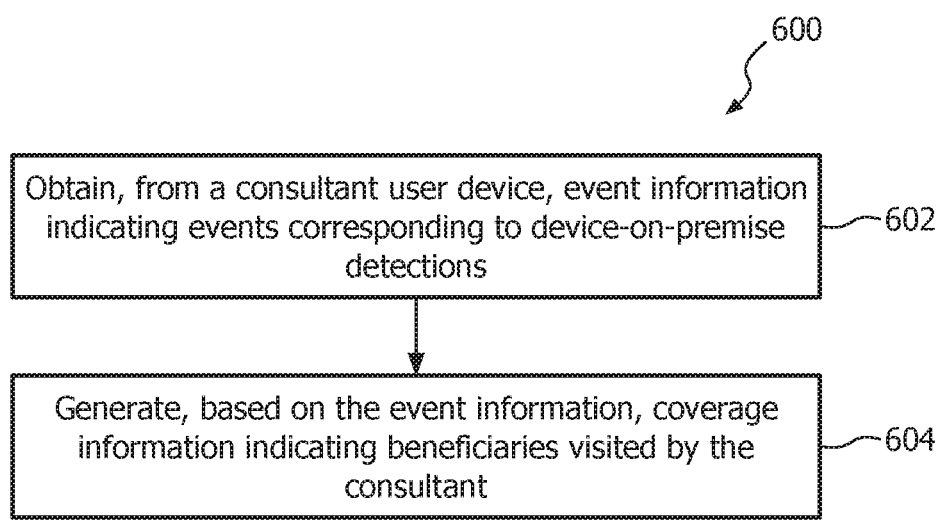
FIG. 6 illustrates a method for generating coverage information based on event information from a consultant user device, in accordance with one or more embodiments.

FIGS. 4-6 comprise example flowcharts of processing operations of methods that enable the various features and functionality of the system as described in detail above. The processing operations of each method presented below are intended to be illustrative and non-limiting. In some embodiments, for example, the methods may be accomplished with one or more additional operations not described, and/or without one or more of the operations discussed. Additionally, the order in which the processing operations of the methods are illustrated (and described below) is not intended to be limiting.

In some embodiments, the methods may be implemented in one or more processing devices (e.g., a digital processor, an analog processor, a digital circuit designed to process information, an analog circuit designed to process information, a state machine, and/or other mechanisms for electronically processing information). The processing devices may include one or more devices executing some or all of the operations of the methods in response to instructions stored electronically on an electronic storage medium. The processing devices may include one or more devices configured through hardware, firmware, and/or software to be specifically designed for execution of one or more of the operations of the methods.

FIG. 4 shows a flowchart of a method 400 of facilitating a user interface via device-on-premise detection and event generation based thereon, in accordance with one or more embodiments.

In an operation 402, event information (indicating events corresponding to device-on-premise detections of one or more beneficiary user devices) may be obtained from the beneficiary user devices. As an example, each of the device-on-premise detections may comprise a detection by at least one of the beneficiary user devices of a location of the at least one beneficiary user device overlapping with a location of at least one service facility premise of a predefined set of service facility premises. Operation 402 may be performed by an event management subsystem that is the same as or similar to event management subsystem 112, in accordance with one or more embodiments.

In an operation 404, a consultant that is to be at a first service facility premise (of the predefined set of service facility premises) may be determined. Operation 404 may be performed by a services management subsystem that is the same as or similar to services management subsystem 114, in accordance with one or more embodiments.

In an operation 406, a set of beneficiaries that are currently at the first service facility premise may be determined based on the event information. As an example, the set of beneficiaries that are currently at the first service facility premise may be determined responsive to determining that the consultant is to be at the first service facility premise. Operation 406 may be performed by an event management subsystem that is the same as or similar to event management subsystem 112, in accordance with one or more embodiments.

In an operation 408, service information (indicating one or more health services previously provided to or requested by beneficiaries of the set of beneficiaries) may be obtained. Operation 408 may be performed by a billing management subsystem that is the same as or similar to billing management subsystem 116, in accordance with one or more embodiments.

In an operation 410, at least a portion of a user interface (indicating beneficiaries to be identified to the consultant) may be generated based on the set of beneficiaries and the service information. Operation 408 may be performed by a presentation subsystem that is the same as or similar to presentation subsystem 118, in accordance with one or more embodiments.

FIG. 5 shows a flowchart of a method 500 of detecting overlap of a user device location and a service facility premise location and generating a corresponding event based thereon, in accordance with one or more embodiments.

In an operation 502, a location of a user device (e.g., beneficiary user device 104, consultant user device 106, etc.) may be obtained at a first time. Operation 502 may be performed by a location subsystem that is the same as or similar to location subsystem 132 or 152, in accordance with one or more embodiments.

In an operation 504, a detection of the obtained location of the beneficiary user device overlapping with a location of at least one service facility premise (of the predefined set of service facility premises) may occur. Operation 504 may be performed by an event subsystem that is the same as or similar to event subsystem 134 or 154, in accordance with one or more embodiments.

In an operation 506, an event corresponding to the detection may be generated. The event may indicate that the user device is detected at the overlapping location at the first time. As an example, the corresponding event may be generated responsive to the overlapping detection. Operation 504 may be performed by an event subsystem that is the same as or similar to event subsystem 134 or 154, in accordance with one or more embodiments.

In an operation 508, event information may be generated such that the event information indicates the event corresponding to the detection. Operation 508 may be performed by an event subsystem that is the same as or similar to event subsystem 134 or 154, in accordance with one or more embodiments.

In an embodiment, with respect to operation 504, the predefined set of service facility premises may be stored at the user device, and the user-device-stored predefined set of service facility premises may be dynamically updated based on the current location of the user device, where a device-on-premise detection of the user device comprising a detection by the user device of a location of the user device overlapping with a location of at least one service facility premise of the dynamically updated predefined set of service facility premises stored at the user device. The dynamic updating operation may be performed by an event subsystem that is the same as or similar to event subsystem 134 or 154, in accordance with one or more embodiments.

FIG. 6 shows a flowchart of a method 600 of generating coverage information based on event information from a consultant user device, in accordance with one or more embodiments.

In an operation 602, event information (indicating events corresponding to device-on-premise detections of a consultant user device) may be obtained from the consultant user device. As an example, each of the device-on-premise detections may comprise a detection by the consultant user device of a location of the consultant user device overlapping with a location of at least one service facility premise of a predefined set of service facility premises. Operation 502 may be performed by an event management subsystem that is the same as or similar to event management subsystem 112, in accordance with one or more embodiments.

In an operation 604, coverage information (indicating beneficiaries visited by the consultant) may be generated based on the event information. Operation 604 may be performed by an event management subsystem that is the same as or similar to event management subsystem 112, in accordance with one or more embodiments.

In some embodiments, the various computers and subsystems illustrated in FIG. 1 may comprise one or more computing devices that are programmed to perform the functions described herein. The computing devices may include one or more electronic storages (e.g., detected event database 122, services database 124, billing database 126, or other electric storages), one or more physical processors 110, 130, 150, or other processors programmed with one or more computer program instructions, and/or other components. The computing devices may include communication lines or ports to enable the exchange of information with a network (e.g., network 170) or other computing platforms via wired or wireless techniques (e.g., Ethernet, fiber optics, coaxial cable, WiFi, Bluetooth, near field communication, or other technologies). The computing devices may include a plurality of hardware, software, and/or firmware components operating together to provide the functionality attributed herein to the servers. For example, the computing devices may be implemented by a cloud of computing platforms operating together as the computing devices.

The electronic storages may comprise non-transitory storage media that electronically stores information. The electronic storage media of the electronic storages may include one or both of system storage that is provided integrally (e.g., substantially non-removable) with the servers or removable storage that is removably connectable to the servers via, for example, a port (e.g., a USB port, a firewire port, etc.) or a drive (e.g., a disk drive, etc.). The electronic storages may include one or more of optically readable storage media (e.g., optical disks, etc.), magnetically readable storage media (e.g., magnetic tape, magnetic hard drive, floppy drive, etc.), electrical charge-based storage media (e.g., EEPROM, RAM, etc.), solid-state storage media (e.g., flash drive, etc.), and/or other electronically readable storage media. The electronic storages may include one or more virtual storage resources (e.g., cloud storage, a virtual private network, and/or other virtual storage resources). The electronic storage may store software algorithms, information determined by the processors, information received from the servers, information received from client computing platforms, or other information that enables the servers to function as described herein.

The processors may be programmed to provide information processing capabilities in the servers. As such, the processors may include one or more of a digital processor, an analog processor, a digital circuit designed to process information, an analog circuit designed to process information, a state machine, and/or other mechanisms for electronically processing information. In some embodiments, the processors may include a plurality of processing units. These processing units may be physically located within the same device, or the processors may represent processing functionality of a plurality of devices operating in coordination. The processors may be programmed to execute computer program instructions to perform functions described herein of subsystems 112-118, 132-134, 152-156, or other subsystems. The processors may be programmed to execute computer program instructions by software; hardware; firmware; some combination of software, hardware, or firmware; and/or other mechanisms for configuring processing capabilities on the processors.

It should be appreciated that the description of the functionality provided by the different subsystems 112-118, 132-134, 152-156, described herein is for illustrative purposes, and is not intended to be limiting, as any of subsystems 112-118, 132-134, 152-156, may provide more or less functionality than is described. For example, one or more of subsystems 112-118, 132-134, 152-156, may be eliminated, and some or all of its functionality may be provided by other ones of subsystems 112-118. As another example, additional subsystems may be programmed to perform some or all of the functionality attributed herein to one of subsystems 112-118, 132-134, 152-156.

Example Embodiments

In an embodiment, a system configured to facilitate a user interface via device-on-premise detection and event generation based thereon may comprise a computer system configured by machine-readable instructions to: obtain, from one or more beneficiary user devices of one or more beneficiaries, event information indicating events corresponding to device-on-premise detections of the one or more beneficiary user devices, each of the device-on-premise detections comprising a detection by at least one of the one or more beneficiary user devices of a location of the at least one beneficiary user device overlapping with a location of at least one service facility premise of a predefined set of service facility premises; determine a consultant that is to be at a first service facility premise of the predefined set of service facility premises; determine, based on the event information, a set of beneficiaries that are currently at the first service facility premise; obtain service information indicating one or more health services previously provided to or requested by beneficiaries of the set of beneficiaries; and generate, based on the set of beneficiaries and the service information, at least a portion of a user interface indicating beneficiaries to be identified to the consultant.

In an embodiment, the system may comprise the one or more beneficiary user devices, where each of the one or more beneficiary user devices comprises one or more physical processors configured by machine-readable instructions to: obtain, via a location subsystem of the beneficiary user device, a location of the beneficiary user device at a first time; detect that the obtained location of the beneficiary user device overlaps with a location of at least one service facility premise of the predefined set of service facility premises; generate an event corresponding to the detection, the event indicating that the beneficiary user device is detected at the overlapping location at the first time; generate at least a part of the event information to indicate the event corresponding to the detection; and provide the at least part of the event information to the computer system.

In an embodiment, at least a beneficiary user device (of the one or more beneficiary user devices) comprises one or more physical processors configured by machine-readable instructions to: dynamically update, based on the current location of the beneficiary user device, the predefined set of service facility premises stored at the beneficiary user device, a device-on-premise detection of the beneficiary user device comprising a detection by the beneficiary user device of a location of the beneficiary user device overlapping with a location of at least one service facility premise of the dynamically updated predefined set of service facility premises stored at the beneficiary user device.

In an embodiment, the one or more physical processors of the computer system are configured by machine-readable instructions to: determine scores associated with beneficiaries of the set of beneficiaries based on the service information, where the determined scores indicate respective relative correlations between health services previously provided to or requested by the beneficiaries of the set of beneficiaries and services available via the consultant, and where generating the portion of the user interface comprises generating actionable areas associated with the indicated beneficiaries such that the actionable areas are arranged on the user interface based on the determined scores.

In an embodiment, the portion of the user interface is provided to a consultant user device of the consultant, and the one or more physical processors of the computer system are configured by machine-readable instructions to: obtain, from the consultant user device, other event information indicating events corresponding to device-on-premise detections of the consultant user device, each of the device-on-premise detections of the consultant user device comprising a detection by the consultant user device of a location of the consultant user device overlapping with a location of at least one service facility premise; and generate, based on the other event information, coverage information indicating beneficiaries visited by the consultant.

In an embodiment, a method for facilitating a user interface via device-on-premise detection and event generation based thereon may be implemented at least in part by a computer system comprising one or more physical processors configured by machine-readable instructions which, when executed, perform the method, the method comprising: obtaining, by the computer system, from one or more beneficiary user devices of one or more beneficiaries, event information indicating events corresponding to device-on-premise detections of the one or more beneficiary user devices, each of the device-on-premise detections comprising a detection by at least one of the one or more beneficiary user devices of a location of the at least one beneficiary user device overlapping with a location of at least one service facility premise of a predefined set of service facility premises; determining, by the computer system, a consultant that is to be at a first service facility premise of the predefined set of service facility premises; determining, by the computer system, based on the event information, a set of beneficiaries that are currently at the first service facility premise; obtaining, by the computer system, service information indicating one or more health services previously provided to or requested by beneficiaries of the set of beneficiaries; and generating, by the computer system, based on the set of beneficiaries and the service information, at least a portion of a user interface indicating beneficiaries to be identified to the consultant.

In an embodiment, the method is further implemented by a beneficiary user device comprising one or more physical processors configured by machine-readable instructions which, when executed, perform the method, the method further comprising: obtaining, by the beneficiary user device, via a location subsystem of the beneficiary user device, a location of the beneficiary user device at a first time; detecting, by the beneficiary user device, that the obtained location of the beneficiary user device overlaps with a location of at least one service facility premise of the predefined set of service facility premises; generating, by the beneficiary user device, an event corresponding to the detection, the event indicating that the beneficiary user device is detected at the overlapping location at the first time; generating, by the beneficiary user device, at least a part of the event information to indicate the event corresponding to the detection; and providing, by the beneficiary user device, the at least part of the event information to the computer system.

In an embodiment, the method is further implemented by a beneficiary user device comprising one or more physical processors configured by machine-readable instructions which, when executed, perform the method, the method further comprising: dynamically update, by the beneficiary user device, based on the current location of the beneficiary user device, the predefined set of service facility premises stored at the beneficiary user device, where a device-on-premise detection of the beneficiary user device comprises a detection by the beneficiary user device of a location of the beneficiary user device overlapping with a location of at least one service facility premise of the dynamically updated predefined set of service facility premises stored at the beneficiary user device.

In an embodiment, the method further comprises determining, by the computer system, scores associated with beneficiaries of the set of beneficiaries based on the service information, the determined scores indicating respective relative correlations between health services previously provided to or requested by the beneficiaries of the set of beneficiaries and services available via the consultant, where generating the portion of the user interface comprises generating actionable areas associated with the indicated beneficiaries such that the actionable areas are arranged on the user interface based on the determined scores.

In an embodiment, the portion of the user interface is provided to a consultant user device of the consultant, and the method further comprises: obtaining, by the computer system, from the consultant user device, other event information indicating events corresponding to device-on-premise detections of the consultant user device, each of the device-on-premise detections of the consultant user device comprising a detection by the consultant user device of a location of the consultant user device overlapping with a location of at least one service facility premise; and generating, by the computer system, based on the other event information, coverage information indicating beneficiaries visited by the consultant.

In an embodiment, a system configured to facilitate a user interface via device-on-premise detection and event generation based thereon may comprise a computer system that comprises: means for obtaining, from one or more beneficiary user devices of one or more beneficiaries, event information indicating events corresponding to device-on-premise detections of the one or more beneficiary user devices, each of the device-on-premise detections comprising a detection by at least one of the one or more beneficiary user devices of a location of the at least one beneficiary user device overlapping with a location of at least one service facility premise of a predefined set of service facility premises; means for determining a consultant that is to be at a first service facility premise of the predefined set of service facility premises; means for determining, based on the event information, a set of beneficiaries that are currently at the first service facility premise; means for obtaining service information indicating one or more health services previously provided to or requested by beneficiaries of the set of beneficiaries; and means for generating, based on the set of beneficiaries and the service information, at least a portion of a user interface indicating beneficiaries to be identified to the consultant.

In an embodiment, the system may comprise a beneficiary user device comprising: means for obtaining a location of the beneficiary user device at a first time; means for detecting that the obtained location of the beneficiary user device overlaps with a location of at least one service facility premise of the predefined set of service facility premises; means for generating an event corresponding to the detection, the event indicating that the beneficiary user device is detected at the overlapping location at the first time; means for generating at least a part of the event information to indicate the event corresponding to the detection; and means for providing the at least part of the event information to the computer system.

In an embodiment, the system may comprise a beneficiary user device comprising: means for dynamically update, based on the current location of the beneficiary user device, the predefined set of service facility premises stored at the beneficiary user device, wherein a device-on-premise detection of the beneficiary user device comprises a detection by the beneficiary user device of a location of the beneficiary user device overlapping with a location of at least one service facility premise of the dynamically updated predefined set of service facility premises stored at the beneficiary user device.

In an embodiment, the computer system further comprises: means for determining scores associated with beneficiaries of the set of beneficiaries based on the service information, where the determined scores indicates respective relative correlations between health services previously provided to or requested by the beneficiaries of the set of beneficiaries and services offered by the consultant, and where the portion of the user interface is generated by generating actionable areas associated with the indicated beneficiaries such that the actionable areas are arranged on the user interface based on the determined scores.

In an embodiment, the portion of the user interface is provided to a consultant user device of the consultant, and the computer system comprises: means for obtaining, from the consultant user device, other event information indicating events corresponding to device-on-premise detections of the consultant user device, each of the device-on-premise detections of the consultant user device comprising a detection by the consultant user device of a location of the consultant user device overlapping with a location of at least one service facility premise; and means for generating, based on the other event information, coverage information indicating beneficiaries visited by the consultant.

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the description provided above provides detail for the purpose of illustration based on what is currently considered to be the most practical and preferred embodiments, it is to be understood that such detail is solely for that purpose and that the disclosure is not limited to the expressly disclosed embodiments, but, on the contrary, is intended to cover modifications and equivalent arrangements that are within the spirit and scope of the appended claims. For example, it is to be understood that the present disclosure contemplates that, to the extent possible, one or more features of any embodiment can be combined with one or more features of any other embodiment.

What is claimed is:

1. A method for facilitating a user interface via device-on-premise detection and event generation based thereon, the method being implemented at least in part by a computer system comprising one or more physical processors configured by machine-readable instructions which, when executed, perform the method, the method comprising:
obtaining, by the computer system, from one or more beneficiary user devices of one or more beneficiaries, event information indicating events corresponding to device-on-premise detections of the one or more beneficiary user devices, each of the device-on-premise detections comprising a detection by at least one of the one or more beneficiary user devices of a location of the at least one beneficiary user device overlapping with a location of at least one service facility premise of a predefined set of service facility premises;
determining, by the computer system, a consultant is at a first service facility premise of the predefined set of service facility premises;
determining, by the computer system, based on the event information, a set of beneficiaries that are currently at the first service facility premise;
obtaining, by the computer system, service information indicating one or more health services previously provided to or requested by at least one beneficiary of the set of beneficiaries;
generating, by the computer system, based on (i) the set of beneficiaries that are currently at the first service facility premise, (ii) the service information, and (iii) the consultant being determined to be at the first service facility premise, at least a portion of a user interface indicating beneficiaries to be identified to the consultant, wherein the generated user interface comprises actionable areas associated with the indicated one or more beneficiaries that, when activated by the consultant via a consultant user device, cause one or more actions to be initiated; and
providing the at least the portion of the generated user interface comprising the actionable areas to the consultant user device.

2. The method of claim 1, wherein the event information is obtained from the one or more beneficiary user devices in response to:
a location subsystem of a beneficiary user device of the one or more beneficiary user device obtaining a location of the beneficiary user device at a first time;
wherein the beneficiary user device: is configured to detect that the obtained location overlaps with the location of at least one service facility premise of the predefined set of service facility premises;
generate an event corresponding to the detection, the event indicating that the beneficiary user device is detected at the overlapping location at the first time;
generate at least a part of the event information to indicate the event corresponding to the detection; and
provide the at least part of the event information to the computer system.

3. The method of claim 1, wherein a beneficiary user device of the one or more beneficiary user devices is configured to:
dynamically update, based on a current location of the beneficiary user device, the predefined set of service facility premises stored at the beneficiary user device, wherein a device-on-premise detection of the beneficiary user device comprises:
a detection by the beneficiary user device of the current location of the beneficiary user device overlapping with the location of at least one service facility premise of the dynamically updated predefined set of service facility premises stored at the beneficiary user device.

4. The method of claim 1, further comprising:
determining, by the computer system, scores associated with the at least one beneficiary of the set of beneficiaries based on the service information, the determined scores indicating respective relative correlations between the one or more health services previously provided to or requested by the at least one beneficiary of the set of beneficiaries and one or more services available via the consultant,
wherein generating the at least the portion of the user interface comprises generating the actionable areas to be arranged on the user interface based on the determined scores.

5. The method of claim 1, further comprising:
obtaining, by the computer system, from the consultant user device, other event information indicating events corresponding to device-on-premise detections of the consultant user device, each of the device-on-premise detections of the consultant user device comprising a detection by the consultant user device of a location of the consultant user device overlapping with a location of at least one service facility premise of the set of service facility premises; and
generating, by the computer system, based on the other event information, coverage information indicating beneficiaries visited by the consultant.

6. The method of claim 3, further comprising:
obtaining, by the computing system and from the beneficiary user device, the dynamically updated predefined set of service facility premises stored at the beneficiary device.

7. A system configured to facilitate a user interface via device on premise detection and event generation based thereon, the system comprising:
a computer system comprising one or more physical processors configured by machine-readable instructions to:
obtain, from one or more beneficiary user devices of one or more beneficiaries, event information indicating events corresponding to device-on premise detections of the one or more beneficiary user devices, each of the device-on premise detections comprising a detection by at least one of the one or more beneficiary user devices of a location of the at least one beneficiary user device overlapping with a location of at least one service facility premise of a predefined set of service facility premises;
determine a consultant is at a first service facility premise of the predefined set of service facility premises;

determine, based on the event information, a set of beneficiaries that are currently at the first service facility premise;

obtain service information indicating one or more health services previously provided to or requested by at least one beneficiary of the set of beneficiaries;

generate, based on (i) the set of beneficiaries that are currently at the first service facility premise, (ii) the service information, and (iii) the consultant being determined to be at the first service facility premise, at least a portion of a user interface indicating one or more beneficiaries to be identified to the consultant, wherein the generated user interface comprises actionable areas associated with the indicated one or more beneficiaries that, when activated by the consultant via a consultant user device, cause one or more actions to be initiated; and provide the at least the portion of the generated user interface comprising the actionable areas to the consultant user device.

8. The system of claim 7, wherein the system further comprises:

the one or more beneficiary user devices, each of the one or more beneficiary user devices comprising one or more physical processors configured by machine readable instructions to:

obtain, via a location subsystem of the beneficiary user device, a location of the beneficiary user device at a first time;

detect that the obtained location of the beneficiary user device overlaps with a location of at least one service facility premise of the predefined set of service facility premises;

generate an event corresponding to the detection, the event indicating that the beneficiary user device is detected at the overlapping location at the first time;

generate at least a part of the event information to indicate the event corresponding to the detection; and provide the at least part of the event information to the computer system.

9. The system of claim 7, wherein the system comprises: the one or more beneficiary user devices, at least a beneficiary user device of the one or more beneficiary user devices comprising one or more physical processors configured by machine-readable instructions to:

dynamically update, based on a current location of the at least one beneficiary user device, the predefined set of service facility premises stored at the at least one beneficiary user device, wherein a device-on-premise detection of the at least one beneficiary user device comprises:

a detection by the at least one beneficiary user device of the current location of the at least one beneficiary user device overlapping with the location of at least one service facility premise of the dynamically updated predefined set of service facility premises stored at the at least one beneficiary user device.

10. The system of claim 7, wherein the one or more physical processors of the computer system are configured by the machine readable instructions to: determine scores associated with the at least one beneficiary of the set of beneficiaries based on the service information, the determined scores indicating respective relative correlations between the one or more health services previously provided to or requested by the at least one beneficiary of the set of beneficiaries and one or more services available via the consultant, wherein the at least the portion of the user interface being generated comprises the machine-readable instructions being configured to generate the actionable areas to be arranged on the user interface based on the determined scores.

11. The system of claim 7, wherein the one or more physical processors of the computer system are configured by the machine readable instructions to:

obtain, from the consultant user device, other event information indicating events corresponding to device-on-premise detections of the consultant user device, each of the device-on-premise detections of the consultant user device comprising a detection by the consultant user device of a location of the consultant user device overlapping with a location of at least one service facility premise of the predefined set of service facility premises; and generate, based on the other event information, coverage information indicating beneficiaries visited by the consultant.

12. The system of claim 7, wherein event information is obtained by the computer system: in response to the one or more beneficiary user devices connecting to the Internet, on a periodic basis, or via one or more triggers.

13. The system of claim 7, wherein the one or more physical processors are further configured by the machine-readable instructions to:

obtain, by the computer system, scheduling information associated with the consultant, wherein the consultant being determined to be at the first service facility is based on the scheduling information associated with the consultant.

14. The system of claim 7, wherein the consultant is determined to be at the first service facility premise responsive to a detection of a consultant user device associated with the consultant being within the first service facility premise.

15. The system of claim 7, wherein the one or more actions comprise at least one of:

causing additional details about an indicated beneficiary to be obtained; or causing a meeting with an indicated beneficiary to be scheduled.

16. The system of claim 15, wherein:

causing the additional details about the indicated beneficiary to be obtained comprises at least one of:

obtaining available services to be offered to the indicated beneficiary, obtaining personal information of the indicated beneficiary, obtaining a medical history for the indicated beneficiary, or obtaining insurance information for the indicated beneficiary; and causing the meeting with the indicated beneficiary to be scheduled comprises sending a message with one or more proposed times for the meeting.

17. The system of claim 7, wherein the consultant being determined to be at the first service facility premise comprises the one or more physical processors being configured by the machine-readable instructions to:

detect a consultant user device of the consultant being within the first service facility premise by obtaining location information from the consultant user device and determining, based on the location information, that a current location of the consultant user device overlaps with a location of the first service facility premise.

\* \* \* \* \*